United States Patent [19]
Scheuermann et al.

[11] Patent Number: 5,136,025
[45] Date of Patent: Aug. 4, 1992

[54] METHOD TO PURIFY BASIC FIBROBLAST GROWTH FACTOR

[75] Inventors: Trina A. Scheuermann, Fremont; S. Joseph Tarnowski, Sunnyvale; Stewart A. Thompson, Mountain View; Kate B. Silverness, Castro Valley, all of Calif.

[73] Assignee: California Biotechnology Inc., Mountain View, Calif.

[21] Appl. No.: 504,435

[22] Filed: Apr. 4, 1990

[51] Int. Cl.$^5$ .................... C07K 3/00; C07K 3/12; C07K 3/18
[52] U.S. Cl. .................... 530/413; 530/350; 530/397; 530/399; 530/412; 530/415; 530/416; 530/412
[58] Field of Search ........... 530/397, 399, 412, 415, 530/416, 417, 750, 413

[56] References Cited

U.S. PATENT DOCUMENTS

| | | | |
|---|---|---|---|
| 4,431,546 | 2/1984 | Hughes et al. | 210/656 |
| 4,569,794 | 2/1986 | Smith et al. | 260/113 |

FOREIGN PATENT DOCUMENTS

| | | |
|---|---|---|
| 3920685 | 9/1985 | Australia . |
| 0275204 | 1/1988 | European Pat. Off. . |
| 0287470 | 4/1988 | European Pat. Off. . |
| 8908117 | 9/1989 | PCT Int'l Appl. . |
| 8908144 | 9/1989 | PCT Int'l Appl. . |

OTHER PUBLICATIONS

Bohlen et al., *Proc. Nat. Acad. Sci. USA*, vol. 81 pp. 5364–5368 (1984).
Hasaharu et al., *Biochem. Biophys. Res. Comm.* (1988) 151:701–708.
Shing, *J. Biol. Chem.* (1988) 263(18):9059–9062.
Ryden et al., *J. Biol. Chem.* (1978) 253(2):519–524.
Chadha et al., *J. Gen. Virol.* (1979) 43:701"706.
Kikuchi et al., *Analyt. Biochem.* (1981) 115:109–112.
Porath, *Archives Biochem. and Biophys.* (1983) 225(2):543–547.
Coppenhaver, *ICRS Med. Sci.* (1985) 13:811–812.
Weselake et al., *Analyt. Biochem.* (1986) 155:193–197.
Sulkowski, *Protein Purification: Micro to Macro* (1987), Alan R. Liss, Inc., pp. 149–162.

*Primary Examiner*—Merrell C. Cashion, Jr.
*Assistant Examiner*—Andrew G. Rozycki
*Attorney, Agent, or Firm*—Morrison & Foerster

[57] ABSTRACT

This invention relates to a method of isolating and purifying proteins such as fibroblast growth factor using metal chelate affinity column chromatography and without the use of heparin. Also disclosed is a method of recovering bFGF multimers and purifying bFGF using metal chelate affinity column chromatography in the absence of heparin.

25 Claims, 5 Drawing Sheets

FIG. 1-1

```
AATTCATGCC TCTTTCTCTC CTTTTGTTGG TAGACGACTT CAGCCTCTGT CCTTTAATTT    60
TAAAGTTTAT GCCCCACTTG TACCCCTCGT CTTTTGGTGA TTTAGAGATT TTCAAAGCCT   120
GCTCTGACAC AGACTCTTCC TTGGATTGCA ACTTCTCTAC TTTGGGGTGG AAACGGCTTC   180
TCCGTTTTGA AACGCTAGCG GGGAAAAAAT GTTGAGTTTA AACTTTTAAA              240
AGTTGAGTCA CGGCTGGTTG CGCACGAAAA GCCCCGCAGT GTGGAGAAAG CCTAAACGTG   300
GTTTGGGTGG TGCGGGGGTT GGGCGGGGGT GACTTTTGGG GGATAAGGGG CGGTGGAGCC   360
CAGGGAATGC CAAAGCCCTG CCGCGGCCTC CGACGCGCGC CCCCGCCCC TCGCCTCTCC    420
CCCGCCCCCG ACTGAGGCCG GGCTCCCCGC CGGACTGATG TCGCGCGCTT GCGTGTTGTG   480
GCCGAAGCCG CCGAACTCAG AGGCCGGACC CAGAAAACCC GAGCGAGTAG GGGGCGGCGC   540
GCAGGAGGGA GGAGAACTGG GGGCGCGGGA GGCTGGTGGG TGTGGGGGGT GGAGATGTAG   600
AAGATGTGAC GCCGCGGCCC GGCGGGTGCC AGATTAGCGG ACGGCTGCCC GCGGTTGCAA   660
CGGGATCCCG GGCGCTGCAG CTTGGGAGGC GGCTCTCCCC AGGCGGCGTC CGCGGAGACA   720
CCCATCTGTG AACCCCAGGT CCCGGGCCGC CGGCTCGCCG GCCACCAGGG GCCGGCGGAC   780
AGAAGAGCGG CCGAGCGGCT CGAGGCTGGG GGACCGCGCG CGCGGCCGCG CGCTGCCGGG   840
CGGGAGGCTG GGGGCCGGG GCCGGGGCCG TGCCCGGAGC GGGTCGGAGG CCGGGGCCGG    900
GGCCGGGGGA CGGCGGCTCC CCGCGCGGCT CCAGCGGCTC GGGGATCCCG GCCGGGCCCC   960
```

FIG. 1-2

```
                                  GCAGGGACC ATG GCA GCC GGG AGC ATC ACC ACG CTG CCC GCC TTG CCC    1008
                                            Met Ala Ala Gly Ser Ile Thr Thr Leu Pro Ala Leu Pro
                                             1                         5                      10

GAG GAT GGC GGC AGC GGC GCC TTC CCG CCC CAC TTC AAG GAC CCC                                       1056
Glu Asp Gly Gly Ser Gly Ala Phe Pro Pro His Phe Lys Asp Pro
 15                      20                      25

AAG CGG CTG TAC TGC AAA AAC GGG GGC TTC TTC CTG CGC ATC CAC CCC                                   1104
Lys Arg Leu Tyr Cys Lys Asn Gly Gly Phe Phe Leu Arg Ile His Pro
 30                      35                      40                  45

GAC GGC CGA GTT GAC GTC CGG GAG AAG AGC GAC CCT CAC ATC AAG                                       1152
Asp Gly Arg Val Asp Val Arg Glu Lys Ser Asp Pro His Ile Lys
         50                      55                      60

CTA CAA CTT CAA GCA GAA GGA GTT GTG TCT ATC AAA GGA GTG                                           1200
Leu Gln Leu Gln Ala Glu Gly Val Val Ser Ile Lys Gly Val
 65                      70                      75

TGT GCT AAC CGT TAC CTG GCT ATG AAG GAA GAT GGA AGA TTA CTG GCT                                   1248
Cys Ala Asn Arg Tyr Leu Ala Met Lys Glu Asp Gly Arg Leu Leu Ala
         80                      85                      90

TCT AAA TGT GTT ACG GAT GAG TGT TTC TTT GAA CGA TTG GAA TCT                                       1296
Ser Lys Cys Val Thr Asp Glu Cys Phe Phe Glu Arg Leu Glu Ser
 95                     100                     105

AAT AAC TAC AAT ACT TAC CGG TCA AGG AAA TAC ACC AGT TGG TAT GTG                                   1344
Asn Asn Tyr Asn Thr Tyr Arg Ser Arg Lys Tyr Thr Ser Trp Tyr Val
110                     115                     120                 125

GCA TTG AAA CGA ACT GGG CAG TAT AAA CTT GGA TCC AAA ACA GGA CCT                                   1392
Ala Leu Lys Arg Thr Gly Gln Tyr Lys Leu Gly Ser Lys Thr Gly Pro
130                     135                     140
```

```
GGG CAG AAA GCT ATA CTT TTT CTT CCA ATG TCT GCT AAG AGC                      1434
Gly Gln Lys Ala Ile Leu Phe Leu Pro Met Ser Ala Lys Ser
            145                     150                 155

TGATTTTAAT GGCCACATCT AATCTCATTT CACATGAAAG AAGAAGTATA TTTTAGAAAT             1494
TTGTTAATGA GAGTAAAAGA AAATAAATGT GTATAGCTCA GTTTGGATAA TTGGTCAAAC             1554
AATTTTTTAT CCAGTAGTAA AATATGTAAC CATGCCCAGT AAAGAAAAAT AACAAAAGTT             1614
GTAAAATGTA TATTCTCCCT TTTATATTGC ATCTGCTGTT ACCCAGTGAA GCTTACCTAG             1674
AGCAATGATC TTTTTCACGC ATTTGCTTTA TTCGAAAAGA GGCTTTTAAA ATGTGCATGT             1734
TTAGAAAACA AAATTTCTTC ATGGAAATCA TATACATTAG AAAATCACAG TCAGATGTTT             1794
AATCAATCCA AAAATGTCCA CTATTTCTTA TGTCATTCGT TAGTCTACAT GTTTCTAAAC             1854
ATATAAATGT GAATTTAATC AATTCCTTTC ATAGTTTTAT AATTCTCTGG CAGTTCCTTA             1914
TGATAGAGTT TATAAAACAG TCCTGTGTAA ACTGCTGGAA GTTCTTCCGG AATTC                 1969
```

FIG.1—3

METHOD TO PURIFY BASIC FIBROBLAST GROWTH FACTOR

TECHNICAL FIELD

The invention relates to a method of isolating and purifying proteins. In particular, the invention relates to a method of isolating and purifying basic fibroblast growth factor which does not require the use of heparin.

BACKGROUND OF THE INVENTION

When tissue has been traumatized, for example by wounding or burning, the healing process is extremely complex but known to be mediated by numerous protein factors. These factors are essential to cell growth and differentiation during the replacement of destroyed tissue. Many factors have been identified as candidate protein factors for healing based on the ability of various tissue extracts (e.g., brain, pituitary, and hypothalamus) to stimulate mitosis in cell culture. A number of acronyms have been given to the factors in these extracts, such as "PDGF" (platelet-derived growth factor), "MDGF" (macrophage-derived growth factor), "EGF" (epidermal growth factor), "TAF" (tumor angiogenesis factor), "ECGF" (endothelial cell growth factor), "FGF" (fibroblast growth factor), "HDGF" (hypothalamus-derived growth factor), "RDGF" (retina-derived growth factor), "HGF" (heparin-binding growth factor). See, e.g., Hunt, T. K., (1984) J- Trauma, 24:S39-S49; Lobb et al., (1984) Biochemistry 23:6295-6299.

Basic fibroblast growth factor (bFGF) was initially isolated from bovine pituitary glands and was identified by its ability to promote fibroblast proliferation. It has since been shown that bFGF acts on a range of cell types. Thus, bFGF has many potential uses including, for example, endothelial cell culture, inducing blood vessel growth, aiding wound healing, etc.

bFGF promotes the proliferation of sensitive target cells, such as vascular endothelial cell and fibroblasts (Gospodarowicz et al., (1987) *Endocr. Rev.*, 8:95–114; Baird et al., (1986) *Recent Prog. Horm. Res.*, 42:143–205). bFGF is chemotactic for a variety of cell types (Moscatelli et al., (1986) *Proc. Nat'l Acad. Sci. U.S.A.*, 83:2091-2095; Senior et al., (1986) *Biochem. Biophys. Res. Commun.*, 141:67-72; Presta et al., (1986) *Mol. Cell. Biol.*, 6:4060–4066), and induces the synthesis of collagenase and plasminogen activator in endothelial cells (Moscatelli et al., supra).

Exogenously supplied bFGF has effects on wound healing (Davidson et al., (1985) *J. Cell Biol.*, 100:1219-1227), bone healing (Canolis et al., (1987) *J. Clin. Invest.*, 79:52-58), vascular grafting (Griesler et al., (1986) *Trans. Am. Soc. Artif. Intern. Organs*, 32:346-349), lens regeneration (Yamada (1982) *Cell Biology of the Eye*, McDevitt D. S. ed., pp. 193-234, Academic Press, New York), and limb regeneration (Gospodarowicz and Mescher (1981) *Advances in Neurology: Neurofibromatosis*, Riccardi V. M. and Mulvihill J. J. eds., Vol. 29, p. 149, Raven Press, New York). Basic FGF is angiogenic "in vivo" (Gospodarowicz et al., (1979) *Exp. Eye Res.*, 28:501-514) and has neurotrophic properties (Morrison et al., (1986) *Proc. Nat'l Acad. Sci. U.S.A.*, 83:7537-7541).

Heparin chromatography has been used to purify native FGF which has been derived from either crude, cell culture-derived lysates or relatively impure commercial preparations. Klagsbrun, M. (1985) Australian Patent Publication AU-A39206/85 discloses application of heparin chromatography to remove undesired impurities from a crude solution of endothelial cell-growth factor (ECG). After the ECG is immobilized on the heparin it is eluted using a salt solution and recovered from the eluate.

Recombinant bFGF has been produced and purified, again, using heparin affinity HPLC. Masaharu et al., (1988) *Biochem. Biophys. Res. Commun.*, 151:701-708. Masaharu et al. used site-directed mutagenesis to change four cysteine residues of the mature bFGF protein to serine residues attempting to stabilize the protein and reduce the heterogeneity of bFGF elution from heparin affinity HPLC, while still retaining biological activity in some of the modified proteins.

Heparin, as used in the known bFGF purification methods, might affect affinity, rate of uptake and pharmacokinetics of bFGF in vitro. If the purified FGF is intended for therapeutic use in vivo, there may be some concern that heparin used to purify FGF could leach into the final product. Because heparin is used clinically to inhibit blood coagulation, it is an undesirable contaminant in therapeutic preparations of bFGF. Furthermore, heparin-Sepharose beads are a soft-bead, agarose gel that, when scaled up for commercial production, collapse under the high pressure used in process scale chromatography. In addition, the heparin purification process yields a product which is only about 95% pure. (Similarly, use of a non-heparin, ion exchange chromatography system to purify basic FGF yielded a product of 95% purity. Banks, EPO publication 275,204.)

Heparin is a critical element in a "biaffinity" purification process as discussed in Shing, (1988) *J. Biol. Chem.*, 263:9059-9062 (hereinafter "Shing"). (See also PCT application WO 89/08117, published 8 Sep. 1989, which is directed to the Shing bFGF purification process as published in 1988; and PCT application WO 89/08144, published 8 September 1989, which is further directed to the purification of urokinase using the Shing biaffinity purification process.) As illustrated by Shing's FIG. 1, the procedure uses the differential affinities of bFGF for heparin and copper ion. After applying a sample containing partially purified bFGF to a column having both heparin and copper ion ligands, the column is washed with 2M NaCl to remove the heparin-bound contaminants while the bFGF remains bound to the copper. When the column is rinsed with 0.6M NaCl the FGF again attaches to both the heparin and the copper. A subsequent wash with 0.6M NaCl and 10 mM imidazole removes the contaminants bound to copper, but FGF, because of its affinity for heparin, remains bound to the column. A gradient of 0.6M NaCl to 2M NaCl plus 10 mM imidazole removes the bFGF forms from the column. Although Shing uses copper to bind bFGF, heparin is, however, half of the column material and so the potential for heparin to leach into the isolated growth factor is still present. (The additional problems of developing a commercially viable scale up and achieving ideal purity are also encountered in the Shing process.)

EPO disclosure 287,470 to Barritault et al. (hereinafter "Barritault"; page number references are to the English translation) shows the purification of growth factors, such as bFGF, using an amino acid derivative column that mimics a heparin column. It uses, e.g., high salt (as in Barritault claim 11) and is an ion exchange type of column. The ligand is prepared by derivatizing —SO₂Cl groups in the presence of MOH, wherein M is a physiologically acceptable metal, with a chosen amino acid to form —SO₃M groups and then —SO₂R groups. (Barritault page 5.) The R group is formed when an amino acid or amino acid derivative is bound to the resin in the presence of the MOH base. (Id.) Although the column may have "biological properties [that] are analogous to those of heparin" (Barritault page 4), the resultant yields are low and the derivatization method is cumbersome.

A number of non-heparin column chromatography systems have been developed for purification of materials other than bFGF. One form of affinity chromatography which does not use heparin is shown in Hughes et al. U.S. Pat. No. 4,431,546 (hereinafter "the '546 patent"). The '546 patent uses ligands of the reactive dye type wherein separation of a biological substance from a mixture is done in the presence of metal ions. See '546 patent, col. 1, lines 42-55. Metal ions are added to the crude solution and the dye is used to bind the desired biological material thereby removing it from the solution so that it may later be eluted in pure form. The metal ions apparently improve binding of the biological material to the ligand. See, e.g., the '546 patent, col. 1, lines 59-65. An inherent problem exists when reactive dyes are used as a ligand for purifying biological material such as FGF destined for use in humans or mammals, given the potential that such dyes are carcinogenic or toxic.

Metal affinity chromatography has not been used to purify bFGF, although various other purification procedures use metal affinity chromatography. See, e.g., Ryden et al., (1978) *J. Biol. Chem.*, 253:519–524; Chadha et al., (1979) *J. Gen. Virol.*, 43:701–706; Kikuchi et al. (1981) *Analyt. Biochem.*, 115:109–112; Porath, J. (1983), *Archives Biochem. and Biophysics*, 225:543–547; Coppenhaver (1985) *ICRS Med. Sci.*, 13:811–812; Weselake et al., (1986) *Analyt. Biochem.*, 155:193–197; Sulkowski, E., (1987) *Protein Purification: Micro to Macro* (Alan Liss, Inc.) pp. 149–162. Those of skill in the metal affinity chromatography field acknowledge that "it is extremely difficult a priori to state which proteins will and which will not exhibit an affinity for immobilized metal ions." Smith, et. al., U.S. Pat. No. 4,569,794 (hereinafter "the '794 patent").

The '794 patent attempts to make protein purification using metal affinity chromatography universally applicable. To achieve this, the is directed to a universal capture peptide which binds to metal ions. Recombinantly produced hybrid molecules of the capture peptide and the peptide of interest are caught. After purification of the hybrid, the capture peptide portion of the hybrid is cleaved from the peptide of interest. Cleavage, however, is not straightforward and may result in either damage to the peptide of interest or may fail to remove undesired residues. Additional purification is then required to separate the peptide of interest from the capture peptide and the uncleaved hybrid. Furthermore, the process is not readily adaptable to purification of nonrecombinant proteins. In sum, although metal ion affinity chromatography has been useful for purifying some proteins, heparin affinity chromatography has been the only sure way to purify bFGF.

An ideal bFGF purification process would provide a method which avoided the use of heparin, yielded a protein that was at least 98% free of contaminating proteins, and could be scaled up for commercial production.

DISCLOSURE OF THE INVENTION

The present invention provides a solution to the problem of purifying bFGF for commercial use; it does not require the use of heparin, thereby alleviating concerns about heparin leaching into the final product; yields a protein that is at least 98% free of contaminants; and can be readily scaled up for commercial production. The invention provides a method for purifying such commercially useful growth factor proteins. The present invention is directed to a method to recover bFGF multimers from a sample containing bFGF, said method comprising applying bFGF capable of multimerization to a metal chelate affinity substrate; eluting from said substrate a multiplicity of fractions, some of which contain multimerized bFGF; and recovering multimerized bFGF from the multimerized bFGF-containing fractions. The present invention is further directed to a method wherein the sample containing bFGF has first been partially purified by contacting an initial sample containing bFGF with a cation exchange matrix under conditions wherein said bFGF is adsorbed to said matrix, followed by eluting said bFGF from the matrix.

The present invention is further directed to a method to purify bFGF from a biological sample, which method comprises contacting said sample containing bFGF to a cation exchange matrix under conditions wherein said bFGF is adsorbed; eluting said bFGF from the matrix to recover a partially purified sample containing bFGF; applying said partially purified bFGF sample to a metal chelate affinity substrate under conditions wherein bFGF is multimerized; eluting from said substrate a multiplicity of fractions, some of which contain multimerized bFGF; recovering multimerized bFGF from the multimerized bFGF-containing fractions; treating said multimerized bFGF with a reducing agent to obtain bFGF monomers; and separating said bFGF monomers from high molecular weight contaminants.

Not only is the method useful for isolating and purifying bFGF, it can be used, e.g., to differentiate mutant forms of bFGF or remove impurities, other proteins, or degradation products from bFGF preparations.

The purification process of the present invention may be briefly summarized as follows. Crude isolates of bFGF can be obtained either by the methods described herein, or using any other suitable means. Furthermore, although the purification process has been developed to isolate bFGF, preferably recombinant human bFGF from *E. coli*, the method can be used to isolate native and recombinant bFGF from any species. The illustrated method uses four separate prototypical chromatography steps. Any separation technique which behaves similarly to the chromatographic methods described herein, including such techniques as mixed-bed resins, membrane technology, batch techniques, etc. can be used.

Depending upon the original degree of purity, a first chromatography step which includes a cation exchanger to which bFGF binds due to its high pI may be usefully employed. bFGF recovered from this first column is approximately 80% pure. Partially purified bFGF is applied to a metal chelate affinity matrix which yields a preparation containing multimeric forms of bFGF and any high molecular weight contaminants. If low molecular weight (MW) contaminants are present an additional chromatography step, which is illustrated by a gel filtration column, uses a size exclusion resin to separate the larger molecular weight species, including bFGF, from smaller molecular weight contaminants. Fractions that contain bFGF are treated to dissociate and chemically reduce the bFGF multimers. The fully dissociated and reduced monomers can then be isolated from any high MW and low MW contaminants. Such isolation may be by means of a column, preferably a gel filtration column that separates monomeric bFGF from higher molecular weight contaminants. Alternatively, other suitable chromatographic systems may be utilized. Pools and pertinent fractions can be analyzed for the presence of the desired protein either using assays described infra or other assay means readily available to those of skill in the art. Preferably, bFGF can be isolated and maintained directly in a buffer suitable to provide a stable pharmaceutical formulation.

BRIEF DESCRIPTION OF THE DRAWINGS

FIG. 1 shows the native DNA sequence encoding, and the deduced amino acid sequence of, human basic FGF.

MODES OF CARRYING OUT THE INVENTION

A. Definitions

Figure 2:
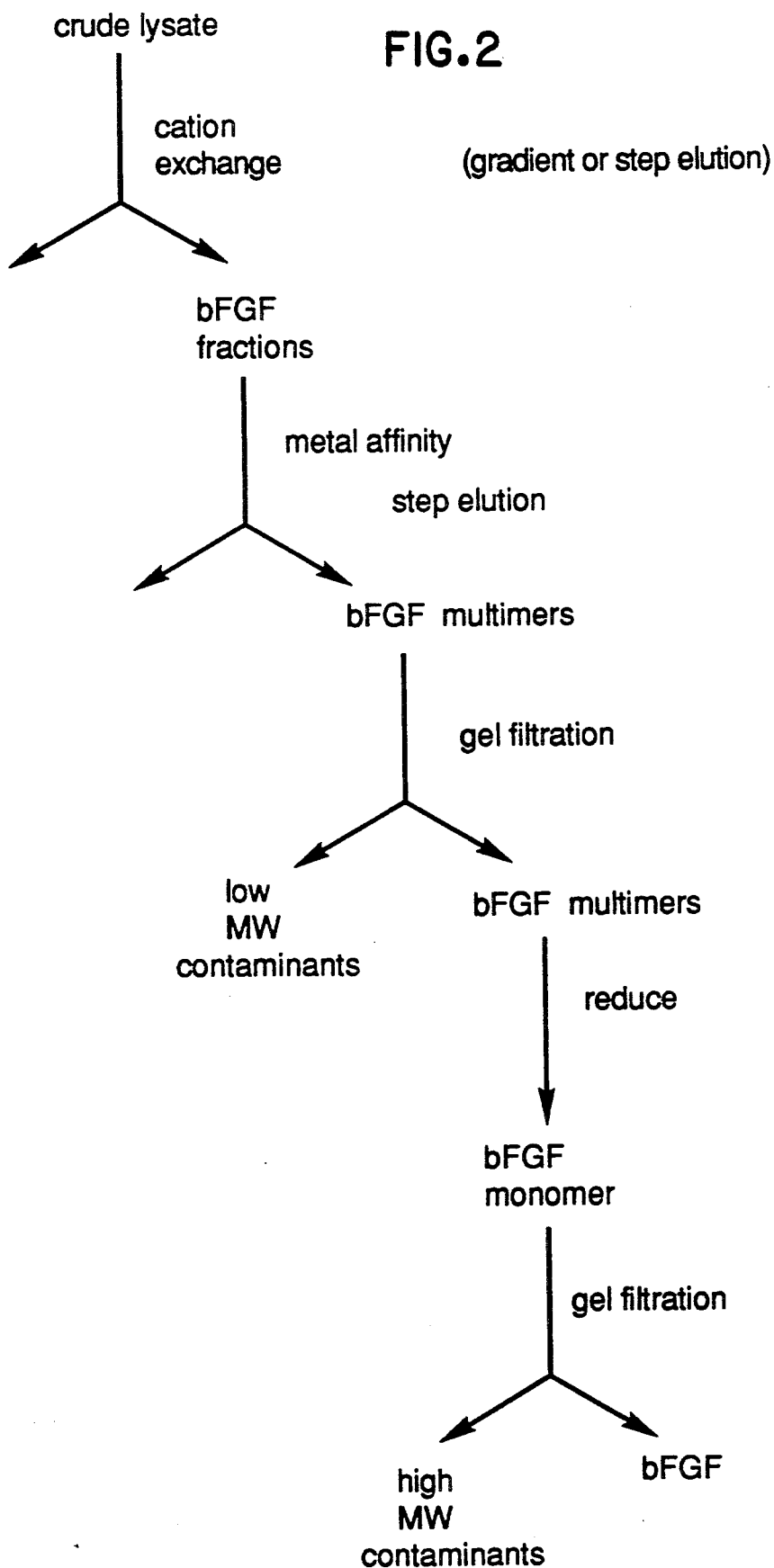
FIG. 2 is a flowchart showing an illustrative purification scheme.

"FGF" means fibroblast growth factor, either acidic or basic, unless otherwise stated, which is either naturally-occurring or produced recombinantly. The FGF will be homologous or substantially homologous to the sequence shown in FIG. 1 (i.e., it will have a similar number of histidine or cysteine amino acid residues). Alternatively, the FGF will have biological activity as shown in the assays herein or in any other assay known to those of skill in the art. Acidic FGF is abbreviated "aFGF"; basic FGF is abbreviated as "bFGF"; human FGF is abbreviated "hFGF."

As used herein "bFGF" means those forms of basic FGF capable of binding to a metal chelate affinity resin. Certain mutant forms of bFGF may be unable to bind to such a resin, at least under certain conditions. Such mutant bFGF forms include those in which the cysteines at positions 78 and 96 are changed to serines. These mutant forms are, of course, minor exceptions to the major population of bFGF which is capable of multimerization via metal chelate ions.

"bFGF multimers" refers to bFGF dimers of about 34 kd and higher bFGF multimers, i.e., trimers, tetramers, etc. having a correspondingly greater molecular weight.

"Lower (or low) molecular weight portion" refers to material below about 34 kd. Such material may comprise bFGF monomers, degraded bFGF, host cell protein, etc.

"Purified" or "pure" refers to material which is free from substances which normally accompany it as found in its native state. Thus "pure" base hFGF, for example, refers to basic hFGF which does not contain materials normally associated with its in situ environment. Of course, "pure" basic hFGF may include materials in covalent association with it, such as glycoside residues. The degree of purity will be at least about 75%, more preferred about 90%, and more preferably at least about 98%.

"Metal chelate affinity substrate" refers to a metal ion in association with a support, such supports comprising a resin, a bead, a particle, a membrane, or other suitable support means.

As used herein the term "mammalian" refers to any mammalian species, but is preferably human.

"Control sequence" refers to a DNA sequence or sequences that are capable, when properly ligated to a desired coding sequence, of effecting its expression in hosts compatible with such sequences. Such control sequences include at least promoters in both procaryotic and eucaryotic hosts, and optionally, transcription termination signals. Additional factors necessary or helpful in effecting expression may also be identified. As used herein, "control sequences" simply refers to whatever DNA sequence may be required to effect expression in the particle host used.

"Operably linked" refers to a juxtaposition wherein the components are configured so as to perform their usual function. Thus, e.g., control sequences or promoters operably linked to a coding sequence are capable of effecting the expression of the coding sequence.

"Cells" or "cell cultures" or "recombinant host cells" or "host cells" are often used interchangeably as will be clear from the context. These terms include the immediate subject cell and, of course, the progeny thereof. It is understood that not all progeny are exactly identical with the parental cell, due to chance mutations or differences in environment. However, such altered progeny are included in these terms, so long as the progeny retain the characteristics relevant to those conferred on the originally transformed cell. In the present case, for example, such a characteristic might be the ability to produce recombinant FGF.

The term "recombinant protein," "recombinant FGF," or "recombinant bFGF" as used herein also refers to analogs of FGF or of bFGF. Such bFGF analogs are described in copending PCT publication WO 88/00198, published 12 Jan. 1989, native human bFGF DNA sequences are shown in FIG. 1 and are described more fully in copending PCT application PCT/US88/02264, filed 3 Jan. 1990, the relevant portions of both of which are incorporated herein by reference. Such analogs include, for example, proteins in which one or more cysteines have been replaced with another amino acid to eliminate sites for intermolecular crosslinking or incorrect intramolecular disulfide bond formation. Conversion of cysteine to neutral amino acids such as glycine, valine, alanine, leucine, isoleucine, tyrosine or methionine is a preferred approach. Serine and alanine are the more preferred replacements because of their chemical homology to cysteine.

B. General Method

1. Initial Source of FGF: Recombinantly Produced Protein

Through utilization of recombinant DNA techniques, a sufficient supply of bFGF can now be manufactured for the repair of traumatized tissue as a result of wounding, surgery, burns, fractures or neurological degeneration.

FGF can be produced by recombinant methods as disclosed in PCT Publication, WO87/01728 published 26 Mar. 1987, the relevant portions of which are incorporated herein by reference. See also Abraham, J., et al., (1986) *Science*, 233:545; Abraham, J., et al., (1986) *The EMBO Journal*, 5:2523.

Briefly, these techniques involve identifying and characterizing the structural gene which encodes the native protein, isolating or synthesizing that gene or a gene encoding a functionally equivalent analog of the native protein, inserting the gene into an appropriate expression vector in a position which permits expression of the gene, transforming competent heterologous hosts, preferably microorganisms, with the vector, identifying correct transformants, and culturing the transformants in a suitable growth medium. The protein is typically recovered from the culture by disrupting the cells, treating the cellular debris with solubilizing agents if necessary (depending on the solubility characteristics of the protein) and one or more extractants to isolate crude protein, and purifying the crude protein by the method of the present invention.

The following general strategy can be used to obtain the sequences that encode these proteins. Most of the techniques that are used to transform cells, construct vectors, extract messenger RNA, prepare cDNA libraries, and the like are widely practiced in the art, and most practitioners are familiar with the standard resource materials. See, e.g., Maniatis et al. *Molecular Cloning* (1982) Cold Spring Harbor Press, which describe specific conditions and procedures. Expression and production of biologically active FGF in yeast is described in Barr et al., (1988) *J. Biol. Chemistry*, 263:16471–16478. Production of human bFGF from *E. coli* is shown in Squires et al., (1988) *J. Biol. Chemistry*, 263:16297–16302. Production of bovine bFGF and bovine FGF analogs in *E. coli* is shown in Fox et al., (1988) *J. Biol. Chemistry*, 263:18452–18458. See also Abraham et al., supra.

The cloned genomic or cDNA sequences can be expressed in appropriate expression systems. cDNA sequences can be provided with appropriate controls suitable for any host, including bacteria, yeast, or eucaryotic cells. Genomic sequences containing introns can be expressed using eucaryotic control sequences in eucaryotic hosts which are capable of splicing the transcripts.

Preparation of the cell lysate may be performed by lysing the cell source at a temperature of about 0° to about 15° C., preferably at about 2° to about 10° C., in a cell lysis buffer of about 0 to about 0.01M EDTA, preferably about 0.01M; about 0.1 to about 0.2M salt, preferably NaCl; about 0.02 to about 0.05M buffer, preferably phosphate, at a pH of about 7 to about 8, preferably about 7.5. Homogenization may be done using any convenient means, one of which comprises a system such as a 30 CD system (Manton-Gaulin, Inc., Everett, Mass.) at about 12,000 to about 15,000 psi, at a flow rate of about 1–3 L/min, to yield 80–90% lysis. Alternatively, the protein may be secreted into the surrounding medium by the host, thereby obviating the cell lysis procedure.

2. Initial Source of FGF: Isolation from Tissue Sources

The bFGF for use in the present invention can also be derived by extraction and subsequent concentration techniques from the pituitary gland of various animals. Many endothelial cell mitogens of 13,000–18,000 molecular weight with a strong affinity for heparin and basic isoelectric point (pI) have been isolated from mammalian sources (see Fox et al., (1988) *J. Biol. Chem.*, 263:18452–18458 for a summary of these mitogens). It is now known that all of these factors are forms of bFGF differing only in the degree of N-terminal processing. As isolated from pituitary tissue, bFGF is a single chain, unglycosylated protein of 16,500 molecular weight.

3. Purification of FGF

Once crude isolates of FGF are obtained by the methods described above, or using any other suitable means, the purification procedure of the present invention can be employed. FIG. 2 shows a flowchart of an illustrative embodiment of the present invention. The preferred method uses four chromatography steps.

An optional first step comprises a cation exchanger to which bFGF binds due to its high pI. Reductant may be included in the cell extraction buffer to destroy or prevent intermolecular disulfide bond formation between FGF molecules or FGF and host cell proteins and to increase the efficiency of binding of FGF to the resin. Cation exchange chromatography is carried out at a temperature of from about 2° to about 25° C., preferably about 4° C. in a buffer of pH of about 6 to about 8, preferably about 7.5. Elution may be stepwise or gradient, preferably stepwise. The column matrix may be comprised of cation exchange resins such as sulfopropyl-Sepharose, sulfonated Sepharose, or carboxymethylcellulose, CM Sephadex, CM Sepharose, CM cellulose, CM silica, Trisacryl, preferably sulfopropyl-Sephadex. *E. coli*-expressed recombinant bFGF recovered from this column is approximately 80 percent pure. Alternatively, any of these cation exchange resins may be bound to a membrane filter to clear the crude isolate and bind bFGF in one step.

The present invention uses metal chelate affinity (preferably copper chelate) to yield a preparation containing multimeric forms of bFGF and high molecular weight contaminants. The metal chelate promotes the formation of FGF multimers presumably by crosslinking free sulfhydryl groups; the interaction of bFGF with metal ions forces it to behave as a high molecular weight aggregate. Although not wishing to be bound by any particular theory, molecular binding was thought to be through metal chelation of histidine groups present in FGF, although binding may be related to the free sulfhydryl groups or disulfide bonds contributed by cysteine residues in the molecule.

Traditional metal chelate affinity resins may be used in the present invention. Alternatively, a suitable support means other than a resin, such as, e.g., a membrane, may be activated to comprise a metal chelate or the support means. For convenience herein, however, traditional resin chromatography will be referred to.

Metal chelate affinity chromatography may be performed at a temperature from about 2° to about 25° C., preferably about 4° C. The equilibration buffer may be 0.0 to about 0.001M imidazole, preferably about 0.0001 to about 0.00005M; about 0.1 to about 1.0M salt, preferably 0.5M NaCl. The column matrix may comprise any chelating resin. Such resins include cellulose, Sepharose, Sepharose Cl-4B, Trisacryl, Silica, or agarose (Fast Flow and cross-linked), with iminodiacetic acid, EDTA or other chelating agents bound to the resin covalently, or other suitable matrices known to those of skill in the art. In addition to copper ions chelated to the resin, other ions (such as cobalt, iron, nickel, zinc, etc.) may be substituted for copper. The use of copper ions provides a convenient visual monitoring of the process due to its bluish color, metal substitutions may offer other advantages, particularly for other proteins. The elution buffer may be about 0.0005M imidazole to about 0.05M imidazole, preferably about 0.01M imidazole, and about 0.1M salt to about 1M salt, preferably about 0.5M NaCl.

The copper column eluate may be concentrated using any convenient means, such as ultrafiltration, and may be diafiltered into the running buffer for the next column, if necessary. Concentration using ultrafiltration is performed at a temperature of about 2° to about 10° C., and may be done using 10,000 molecular weight cut off (MWCO) membranes to a final concentration of about 10 to about 40 mg/ml of protein.

The next step is to remove the low molecular weight contaminants, degraded FGF, and host cell proteins. This may be done using any convenient means known to those of skill in the art that can isolate bFGF multimers, preferably gel filtration chromatography, which uses a size exclusion resin to separate the larger molecular weight species, including bFGF multimers, from smaller molecular weight contaminants. (Other means include, but are not limited to, ultrafiltration with suitable exclusion membranes and hydrophobic techniques.) Suitable matrixes comprise Sephacryl S-200, Superose 12, Sepharose S-300, Superdex, Trisacryl, acrylamide, Sephadex or similar resins known to those of skill in the art which are capable of fractionating the sample in the desired size range. Gel filtration may be carried out at a temperature of about 2° to about 25° C., preferably about 4° C. A suitable buffer comprises about 0.1 to about 1.0M salt, preferably NaCl; 0.0 to about 0.005M EDTA, preferably about 0.001M EDTA; at a pH of about 7 to about 8, preferably about pH 7.5. Those of skill in the art will be able to optimize the buffer used with a particular resin. The peak that represents FGF is pooled and treated with a suitable reductant to dissociate the FGF multimers. For example, dithiothreitol (DTT) is generally added in about a 10M excess to sulfhydryl groups estimated to be present in the protein; DTT and EDTA may further serve to remove any copper that is bound to FGF. Reduction is done at a temperature of about 2° to about 40° C., preferably about 20° C.; at a pH of about 7 to about 9, preferably about pH 7 to about 8, for a period of about 0.5 to about 30 hours, preferably about 12 to about 24 hours. Other means of dissociation that can be used include addition of 2-mercaptoethanol, cysteine, cystamine, glutathione, dithioerythiol, or other well-known reducing agents.

The monomeric form of FGF may be removed from the mixture using any convenient means known to those of skill in the art, which means can isolate bFGF monomers. For example, the pooled fraction may be recovered via a gel filtration column, ultrafiltration, hydrophobic or ion exchange separation techniques, (or any other suitable chromatographic system known to those of skill in the art that can distinguish dimers or other multimers from monomeric bFGF) in order to separate the remaining multimeric forms of bFGF from the monomeric, bioactive bFGF. Gel filtration may be done at a temperature of about 2° to about 25° C., preferably about 4° C. The buffer comprises about 0.0 to about 1.0M salt, preferably NaCl; 0.0 to about 0.01M EDTA, preferably about 0.001M; and is buffered to a pH of about 5 to about 7, preferably about pH 6.5. Those of skill in the art will be able to optimize the buffer composition to achieve best separation with other means than size exclusion resins. Alternatively, monomeric bFGF from the previous step may be placed in a buffer suitable to provide a stabilized bFGF formulation, such as mannitol, sucrose, lactose, aspartic acid, etc. Stabilizers useful in the invention are metal chelating agents, for example EDTA, as described in U.S. patent application Ser. No. 07/504,340, (attorney docket 1900-0268), and all other references herein, the contents of which, are incorporated by reference. In addition, use of an appropriate resin or ultrafiltration for exchange of bFGF from high salt to a lower salt concentration may be required. The column matrix may comprise Sephacryl 200, Superose 12, Sephadex G-100, or similar resins familiar to those of skill in the art.

Alternatively, after metal chelate chromatography, reducing agent can be added to multimerized bFGF, then low molecular weight contaminants removed and FGF monomers isolated in a single step. Suitable chromatography resins for this procedure may include size exclusion; ion exchange; or other hydrophobic separation techniques.

Finally, a mixed bed resin containing both cation exchanger and metal chelate affinity chromatography may be used to purify bFGF. A crude lysate containing bFGF would be added to the mixed bed resin in a buffer comprising a high salt concentration, for example about 1M NaCl and low imidazole (for example about 0.0001 to about 0.00005M). The bFGF would bind to the metal but not to the cation exchanger. A subsequent wash would comprise a high imidazole (for example about 5 mM) and a low salt (for example about 0.1M NaCl) Such a wash would cause multimerized bFGF to be released from the metal and bind to the cation exchanger, while other contaminants would be washed away. Finally, a high salt, high imidazole (for example about 0.0005M to about 0.05M imidazole and about 0.5 to about 1.0M NaCl) wash would release the bFGF multimers from the mixed bed resin.

Pools and pertinent fractions can be analyzed for purity and biological activity using assays described infra.

4. Tests for Contaminants

Activity of bFGF after purification can be determined by a variety of assays, such as the adrenal cortical endothelial cell assay (ACE assay) or the baby hamster kidney-21 (BK)-21 microtiter cell proliferation assay. Additionally, tests for contamination of the final product are intended to monitor purity, such as limulus amebocyte lysate (LAL) assay, residual nucleic acid contamination range, *E. coli* host cell protein assay, and assay for pyrogens.

C. Examples

The following examples are intended to illustrate but not to limit the invention.

Example 1

Expression of Recombinant FGF Construction of Plasmid pTSF11

A. Human Basic Fibroblast Growth Factor

Bovine basic FGF cDNA was used to develop hybridization probes to isolate basic FGF clones from human cDNA and genomic libraries as described in U.S. Ser. No. 869, 382, filed 30 Aug. 1986, Abraham, J. A. et al., *Science* (1986) supra, and Abraham, J. A. et al., *The EMBO Journal* (1986) supra, all of which are incorporated herein by reference.

There are only two amino acid differences between basic bovine FGF and human FGF, at position 121, where the bovine protein has Ser and the human protein has Thr, and at position 137, where the bovine protein has Pro and the human has Ser. These differences are the result of a single nucleotide difference in each case; therefore, bovine cDNA may conveniently be modified by site directed mutagenesis as described below to encode the human protein, and, indeed, standard site-specific mutagenesis techniques were used to alter these codons. The lambda BB2 clone (ATCC No. 40196) was digested with EcoRI and the 1.4 kb region spanning the bFGF protein-encoding portion was ligated into the EcoRI site of M13mp8 and phage carrying the insert in the correct orientation were recovered. The in vitro mutagenesis was carried out in the presence of three oligonucleotides: the "universal" primer, a 17-mer; the mutagenic 16-mer 5'-GAAATACACCAGTTGG-3'; which alters the coding sequence at codon 123, and the mutagenic 17-mer 5'-ACTTGGATCCAAAACAG-3', which alters the sequence at codon 137. The mutagenized phage was also subjected to a second round of in vitro primer-directed mutagenesis to create a HindIII site 34 bp downstream from the translation termination codon using the mutagenic 25-mer, 5'-TTTTACAT-GAAGCTTTATATTTCAG-3', The resultant mutated DNA was sequenced by dideoxynucleotide sequence analysis (Sanger et al., supra) to confirm that the desired mutagenesis had occurred, and the approximately 630 bp fragment spanning the FGF coding region was excised with HindIII and ligated into HindIII digested pUC13 to obtain the intermediate plasmid pJJ15-1.

B. Construction of Gene with Synthetic Coding Region for N-terminal End of FGF Gene In order to lower the G+C content of the 5' end (the first 125 base pairs) of the coding region contained in pJJ15-1, a synthetic DNA fragment was constructed with the sequence shown below using the following synthetic oligonucleotides. The oligonucleotides were annealed in pairs, ligated together sequentially, and ligated into HindIII cut m13mp9. The sequence of the synthetic 125 bp insert in mp9 was confirmed by dideoxy sequencing. The NdeI to HhaI subfragment of the synthetic insert was isolated, joined to the 377 base pair, HhaI-to-HindIII DNA fragment from JJ15-1 that spans approximately the carboxy-terminal three quarters of the basic FGF coding sequence, and then ligated into the NdeI and HindIII sites of the expression vector pTrp-233 to yield the plasmid pTFS11.

Oligonucleotides:

| Number | Sequence |
|---|---|
| 1670 | 5'-pAGCTTCATATGGCTGCTGGTTCTATCACTACC |
| 1623R | 5'-pCTGCCAGCTCTGCCAGAAGACGGTGGTT |
| 1624R | 5'-pCTGGTGCCTTCCCACCAGGTCACTTCAA |
| 1625R | 5'-pAGACCCAAAACGTCTGTACTGCAAAAAC |
| 1680 | 5'-pGGTGGTTTCTTCCTGCGCA |
| 1679 | 5'-pTAGAACCAGCAGCCATATGA |
| 1622 | 5'-pTCTTCTGGCAGAGCTGGCAGGGTAGTGA |
| 1619 | 5'-pACCTGGTGGGAAGGCACCAGAACCACCG |
| 1626 | 5'-pAGTACAGACGTTTTGGGTCTTTGAAGTG |
| 1673 | 5'-pAGCTTGCGCAGGAAGAAACCACCGTTTTTGC |

Construction of Synthetic Gene for the Amino Terminal Region of bFGF:

```
HindIII  NdeI 10          20          30          40          50
AGCTTCATATG  GCTGCTGGTT  CTATCACTAC  CCTGCCAGCT  CTGCCAGAAG
    AGTATAC  CGACGACCAA  GATAGTGATG  GGACGGTCGA  GACGGTCTTC 60          70          80          90         100
ACGGTGGTTC  TGGTGCCTTC  CCACCAGGTC  ACTTCAAAGA  CCCAAAACGT
TGCCACCAAG  ACCACGGAAG  GGTGGTCCAG  TGAAGTTTCT  GGGTTTTGCA HhaI
        110         120         130
CTGTACTGCA  AAAACGGTGG  TTTCTTCCTG  CGCA
GACATGACGT  TTTTGCCACC  AAAGAAGGAC  GCGTTCGA
```

C. Preparation of Expression Vector for Mutagenized Gene Inserts

The HindIII site of the polylinker region of plasmid pUC9 was removed so as to facilitate subcloning mutated DNA into the final expression vector. Approximately 5 ug of pUC9 (New England Biolabs) was digested with HindIII (20 units; New England Biolabs) according to the manufacturers instructions in 0.05 ml. The reaction was then supplemented with 0.5 mM dNTPs and the Klenow fragment of DNA Polymerase I (5 units; Boehringer Manheim) and incubated for 30 minutes at 15° C. The reaction was then extracted twice with an equal volume of phenol/chloroform (1/1), twice with chloroform, made 0.2M NaCl, and then precipitated with two and a half volumes of ethanol. The precipitate was collected by centrifugation (15,000 g in a Microfuge at 4° C.), lyophilized, and then incubated in 0.1 ml with 1X kinase ligase buffer, 1 mM ATP, and T4 DNA ligase (20 units; New England Biolabs) for 4 hours at 12° C.

An aliquot of the reaction (0.01 ml) was then used to transfect competent MC1061 cells. The transfected bacteria were grown overnight on L agar plates supplemented with 100 ug/ml ampicillin. DNA was isolated from 6 colonies by the alkaline lysis procedure and tested for the loss of the HindIII site. A bacteria containing the plasmid, pUC9delH3-1, was isolated. The plasmid DNA was prepared and 10 ug was digested in 0.4 ml with PvuI (20 units; New England Biolabs) and EcoRI (50 units; New England Biolabs) for 2 hours according to the manufacturers instructions. The reaction was then extracted twice with an equal volume of phenol/chloroform (1/1) and twice with an equal volume of phenol and then precipitated with isopropanol. The precipitate was collected by centrifugation, washed with 70% ethanol, lyophilized, resuspended in 0.008 ml water and the ~2.07 kb PvuI-EcoRI fragment of pUC9delH3-1 (designated fragment A) containing the origin of replication was isolated by acrylamide gel electrophoresis.

Concurrently pTSF11 DNA (10 ug) was incubated with PvuI (10 units) and EcoRI (10 units) in 0.15 ml for 1 hour at 37° C. according to the manufacturers directions and collected as described above. The ~1.3 kb PvuI-EcoRI fragment of pTSF11 containing the Trp promoter/operator region, FGF coding region and the transcription termination sequences, designated fragment B of pTSF11, was isolated by polyacrylamide gel electrophoresis and ligated to the ~2.07 kb PvuI-EcoRI fragment A of pUC9delH3-1, and used to transfect competent $E.\ coli$ HB101 cells. The bacteria were grown overnight on L agar plates supplemented with 100 ug/ml ampicillin. Plasmid DNA from one recombinant, pUC9delH3-pTSF-3, was isolated and shown to contain the expected restriction map (HindIII cuts the plasmid only once; the sizes of HindIII-EcoRI, HindIII-PvuI and HindIII-PstI fragments are approximately 560 and 2900, 800 and 2700, and 560 and 2900 bp respectively DNA from the plasmid pUC9delH3-pTSF-3 was isolated and 200 ug incubated in 1.0 ml with 100 units of HindIII, 100 units of EcoRI, 5 mM spermidine for 4 hours at 37° C. according to the manufacturers instructions. The reaction was butanol extracted to reduce the volume to 0.7 ml and then extracted with phenol/chloroform and chloroform as described above. The DNA was collected by ethanol precipitation and the ~2.9 kb HindIII-EcoRI fragment containing the ampicillin resistance gene, the origin of replication and the two transcription stop signals, designated fragment C of pUC9delH3-pTSF-3, was isolated by two sequential runs on polyacrylamide gels. This vector fragment serves as the preferred vector for expressing any of the DNA which has been altered by in vitro mutagenesis.

Plasmid pUC9-pTSF11, a vector closely resembling plasmid pUC9delH3-pTSF-3 but containing an intact HindIII site in the multiple site polylinker region, can also be used as a preferred vector for expressing both recombinantly produced FGF (all forms) and any of the analogs of the present invention. This vector was constructed by individually digesting plasmids pUC9 and pTSF11 with PvuI and EcoRI, isolating the ~2.07 kb PvuI-EcoRI vector fragment from pUC9 and the ~1.3 kb PvuI-EcoRI fragment containing the trp promoter/operator region, FGF coding region, and the transcription termination sequences from pTSF11, and ligating the two isolated fragments. This vector can then be used to express the FGF analog gene sequences as taught with pUC9-pTSF11 by inserting the HindIII-EcoRI DNA cassettes into the appropriately digested vector and transforming $E.\ coli$ bacterium.

EXAMPLE 2

Purification of Recombinant Human bFGF from $E.\ coli$

The fermentation broth was taken from the fermenter and centrifuged at 4000×g for 30 minutes at 4°-8° C. to recover whole cells. The cell pellets were washed, packaged, and stored at −80° C. The purification process was carried out at 4°-25° C. unless otherwise specified. The frozen cell mass was suspended with a Tekmar mixer in 4 volumes of lysis buffer (0.05M NaPi, pH 7.5, 0.1M NaCl, 0.01M EDTA, 0.005M DTT). The cell suspension was passed twice through a Manton-Gaulin homogenizer at 2 liters per minute under 15,000 psi. The resulting crude cell extract was clarified by low speed centrifugation (5000×g for 1 hour) and microfiltration with a 0.2 micron Durapore membrane from Millipore, or an equivalent. (If necessary, this material can then be concentrated by ultrafiltration before loading the first column.)

The first column used in purification of FGF from the majority of other proteins in the crude cell extract was a cation exchanger, sulfopropyl-Sephadex C25 (Pharmacia). The column was prepared for use with sequential washes of 0.5M sodium hydroxide in pyrogen-free water, 0.5M HCl and pyrogen-free water, and equilibrated in sodium phosphate pH 7.5; 0.1M NaCl (IEX Buffer #1). (All buffers in this example were made by dissolving the proper components in pyrogen-free water, and their pH adjusted with either aqueous stock sodium hydroxide or hydrochloric acid when at 2°-8° C.) The conductivity of the crude cell extract was adjusted to equal the equilibration buffer with 5M sodium chloride before loading onto the column. The unbound proteins were washed from the column with IEX Buffer #1 until a stable baseline was achieved. Elution of the bound proteins was performed with 0.05M sodium phosphate, pH 7.5, from about 0.1 to 0.5M sodium chloride in a stepwise gradient. The 0.5M eluate containing bFGF was pooled and applied to the next column in the purification scheme.

The next step utilized metal affinity chromatography. The column used, iminodiacetate Sepharose Fast-Flow, was equilibrated with 0.02M sodium phosphate pH 7.5, 0.5M sodium chloride, 0.0005M imidazole (MCA Buffer #1), after being regenerated sequentially with 0.005M EDTA, pyrogen-free water, cupric sulfate (5 mg/ml), pyrogen-free water, and 0.02M sodium phosphate pH 7.5, 0.5M sodium chloride, 0.01M imidazole. Proper amounts of imidazole and sodium chloride were added to the FGF-containing ion exchange eluate to bring it to 0.0005M and 0.5M, respectively. After loading the sample onto the column, the column was thoroughly washed with 0.02M sodium phosphate, pH 7.5, 0.5M NaCl, and 0.0005M imidazole. The column was subsequently eluted with 0.02M sodium phosphate pH 7.5, 0.5M sodium chloride, 0.01M imidazole, and the eluate containing bFGF was then concentrated by ultrafiltration to approximately 50 mg of protein/ml.

In the next step, a gel filtration column comprising Superose 12 was used to separate the larger molecular weight species, which include bFGF multimers, from the smaller molecular weight contaminants. The running buffer was 0.02M sodium phosphate pH 7.5, 1M sodium chloride, 0.001M EDTA, and the sample load volume equal to up to 5% of the total column volume. The broad peak that eluted at approximately 65% column volume was pooled and treated overnight at 2°-25° C. with DTT in a 10 molar excess over sulfhydryl groups in the protein. The pool was concentrated to up to 50 mg/ml, and passed over a second Superose 12 gel filtration column (up to 5% load volume) equilibrated with running buffer containing 0.02M sodium phosphate pH 6.5, 1M sodium chloride, 0.001M EDTA. The protein of interest (bFGF monomer) eluted at approximately 75% of total column volume. The peak was pooled, analyzed, aliquotted, and stored at −80° C. until further use.

All pools and pertinent fractions were analyzed by the Pierce BCA (Bicinchoninic Assay) protein assay for total protein (Smith, P. K., et al., (1985) *Anal. Biochem.*, 150:76–85), by 15% SDS-PAGE (Laemmli, (1970) *Nature*, 227:680–685), loading the equivalent of 10 ug of protein in each lane, and by heparin HPLC for quantitation. The gels were stained with Coomassie blue or silver, using standard techniques (see, e.g., Merril, et al., (1982) *Electrophoresis*, 3:17–23). Other in vitro bioassays were performed on the final product, such as amino acid composition analysis, N-terminal sequence, Western blots, tryptic maps, and bovine adrenal cortex capillary endothelial cell (ACE) cell proliferation assay (Esch, F. et al. (1985) *Proc. Nat'l Acad. Sci.*, 82:6507–6511). This ACE assay was used as a measure of the potency (percent activity or relative specific activity), of the recombinant bFGF.

Typical Recovery and Yield

Table 1 shows the total protein recovered at each step of purification for three different lots of bulk bFGF. The bFGF content at the start of purification was estimated by SDS-PAGE densitometry scanning and confirmed by using an affinity assay based on the binding of bFGF to heparin-Sepharose or heparin TSK HPLC. Briefly, an aliquot of cells was extracted and applied to heparin-Sepharose, and eluted with an increasing salt gradient. The peak area of bound protein was determined. This number was then used to calculate a bFGF concentration from a standard curve. Typically, expression levels in *E. coli* cells range from about 7% to 10% of total protein in an extract.

TABLE 1

Yield Summary of bFGF Purification

| STEP | Batch[1] | | | | | |
|---|---|---|---|---|---|---|
| | FG10-89-90 | | FG11-89-82 | | FG01-90 | |
| | Protein (g) | bFGF[2] (g) | Protein (g) | bFGF (g) | Protein (g) | bFGF (g) |
| 1. Crude extract | 311.0 | 24.9 | 391.0 | 31.3 | 320.0 | 25.6 |
| 2. SP-Sephadex | 13.4 | — | 17.5 | — | 10.8 | — |
| 3. Copper chelate | 10.3 | — | 12.7 | — | 6.6 | — |
| 4. Gel Filtration I | 6.4 | — | 8.8 | — | 3.6 | — |
| 5. Gel Filtration II[3] | 3.2 | 3.2 | 4.3 | 4.3 | 2.8 | 2.8 |

[1]Each batch was derived from approximately 2 Kg wet cell weight of *E. coli*.
[2]bFGF was determined in the initial extract by purifying an aliquot on heparin-Sepharose affinity resin and determining peak area of the salt eluted fraction.
[3]Protein was determined by the BCA assay (Smith, P. K., et al., (1985) Anal. Biochem, 150:76–85) using bovine serum albumin as a standard. Other protein determinations were made using the Bradford dye binding assay.

Table 2 is an example that shows an analysis of each step using the ACE bioassay (Esch, et al., (1985) *Proc. Nat'l Acad. Sci.*, 82:6507–6511). Each column eluate was active, and no statistically significant differences were observed between the ion exchange eluate and later process steps. The recovery of units of bFGF activity at each step was consistent with bFGF protein recoveries estimated by SDS-PAGE, within assay variation.

TABLE 2

Summary of Biological Activities of Process Intermediates

| Step | Total[1] Protein (g) | Biological activity | | Total[3] Units (×10$^9$) | Specific Activity (u/mg × 10$^6$) |
|---|---|---|---|---|---|
| | | ED$_{50}$ (pg/ml) | Per-cent[2] | | |
| 1. Crude extract | 212 | nd | nd | nd | nd |
| 2. SP-Sephadex | 13.3 | 255 | 111 | 32.6 | 2.5 |
| 3. Copper chelate | 2.7 | 240 | 118 | 7.0 | 2.6 |
| 4. First Superose | 1.7 | 245 | 116 | 4.3 | 2.6 |
| 5. Second Superose | 1.3 | 378 | 75 | 2.1 | 1.7 |

[1]Protein was determined by BCA assay (Smith, et al., supra) using bovine serum albumin as a standard.
[2]Biological activity (Esch, et al., supra) is reported as percent of the ED$_{50}$ value determined for reference standard of bFGF with the ACE assay. All other samples were assayed together and corrected with the same value.
[3]One unit of reference standard activity is defined as the amount required to give half-maximal stimulation of ACE cell proliferation; the number of units in each of the purification steps was determined relative to the reference standard.
nd = not determined

EXAMPLE 3

Determination of Residual Copper Ion in Purified bFGF

The following procedure illustrates the procedure used to determine the amount of residual copper. Samples were taken during the purification of bulk Lot #FG001 after each column chromatography step (ion exchange, metal chelate, gel filtration I and final bulk protein). Two other bulk bFGF lots were analyzed to determine the range in residual copper values. The protein content of each sample was determined by a BCA assay using bovine serum albumin as a standard. Bulk lots were adjusted to 5 mg/ml bFGF before assaying. As a control, samples of corresponding buffers were tested in parallel.

Sample Preparation

Protein samples were prepared for atomic absorption by hydrolysis with 0.1M $HNO_3$ and $H_2O_2$ at 80° C. Dilutions were performed as necessary to bring samples into the working range of the assay. Readings were done in an atomic absorption furnace upon 0.1 ml of acid hydrolyzed sample. The working range of the assay was between 0.005 and 0.5 ug/ml, with an absolute detection limit of 0.0008 ug/ml. A standard curve was done between 0.001 and 0.5 ug/ml. Duplicate or triplicate determination were done on all samples. Interference was tested by performing a known addition to each protein sample. No interference was observed in this experiment.

Data are reported as micrograms of copper per ml of solution (ppm) and as micrograms of copper per milligram of protein.

Table 3 shows results from one experiment performed as described. Before the metal chelate step, the pool contained about 0.2 ug copper per milligram of protein. Copper content increased by fourfold per milligram protein during the metal chelate column step. The remainder of the process removed 96% of detectable copper, and the final pool contained significantly less copper than the sample prior to the metal chelate step. Standard deviations of triplicate determinations averaged 15%. All buffers that were tested contained very low levels of copper.

TABLE 3

Determination of Copper Content in bFGF Samples

| Sample | Copper content ppm (ug/ml) | Protein mg/ml | Copper content ug/mg protein |
|---|---|---|---|
| Lot #FG001 | | | |
| Ion exchange | 0.117 ± .026 | 0.56 | 0.21 |
| Buffer control | 0.017 ± .002 | | |
| Metal chelate pool | 1.47 ± .37 | 1.65 | 0.89 |
| Buffer control | 0.018 ± .005 | | |
| Superose I pool | 1.75 ± .019 | 4.0 | 0.44 |
| Buffer control | 0.011 ± .001 | | |
| Bulk pool, Lot #FG001 | 0.180 ± .014 | 5.0 | 0.04 |
| Bulk pool, Lot #FG004 | 0.060 ± .003 | 5.0 | 0.01 |
| Bulk pool, Lot #FG002 | 0.161 ± .019 | 5.0 | 0.03 |
| Buffer control | 0.006 ± .003 | | |

Average of 3 bulk lots: 0.03 ug/mg bFGF ± .01
Estimated copper clearance factor: (.89 ug/mg-.04 ug/mg) % .89 ug/mg = 96%

In conclusion, the data indicate that the copper content of the process pool increased during metal chelate affinity chromatography. The subsequent process steps removed the added copper, and the level detected in three lots of bulk bFGF was consistent and was well below that detected prior to metal chelate affinity chromatography. The copper level in bulk bFGF ranges from 0.06 to 0.18 ug/ml, which is significantly below the normal human serum level.

EXAMPLE 4

Physicochemical Characterization of bFGF

This section describes the physicochemical methods used to characterize bFGF. Data is shown for three separate lots, numbered "1," "2," and "3."

Amino Acid Composition Analysis

Amino acid compositional analyses have been performed for three lots of bFGF (1, 2, 3) using a Hewlett-Packard 1090M HPLC-based AminoQuant system. This was operated according to the manufacturer's instructions. Samples were dried under vacuum in a glass microtube (Waters Associates, Bedford, Mass.), then hydrolyzed with vapor phase 6N HCl for 16 hours in a nitrogen atmosphere using the Pico-Tag workstation. After drying under vacuum, the samples were redissolved and derivatized with OPA (o-phthalaldehyde) and FMOC (9-fluroenylmethyl chloroformate) immediately prior to injection in the analyzer. Tryptophan and cysteine are not measured using this procedure.

All chemicals and columns used for the derivatization and analysis were purchased from Hewlett-Packard and used according to their instructions. All data were collected and processed by the onboard computer in the analyzer using software supplied with the instrument.

The results of performing an amino acid analysis after acid hydrolysis of bFGF are summarized in Table 4. The computer predicted molecular weight for bFGF is 17,124 daltons, using 154 amino acids (no amino-terminal methionine) for the calculation. By adding the mass of one tryptophan and four cysteines to the calculated molecular weight for each lot of bFGF, the molecular weight obtained was within five percent of the predicted value.

TABLE 4

Amino Acid Composition of bFGF[1]

| Amino Acid | Molecular Weight | Moles Expected | Lot #3 Moles Observed | Lot #2 Moles Observed | Lot #1 Moles Observed |
|---|---|---|---|---|---|
| Alanine | 89.09 | 11 | 11.1 | 11.9 | 11.2 |
| Arginine | 174.2 | 11 | 11.7 | 12.4 | 11.7 |
| Asparagine | 132.12 | 12 (as ASX) | 12.6 | 10.8 | 12.6 |
| Aspartic Acid | 133.10 | — | — | — | — |
| Cysteine | 121.15 | 4 | N.D. | N.D. | N.D. |
| Glutamine | 146.15 | 12 (as GLX) | 11.5 | 12.4 | 12.9 |
| Glutamic Acid | 147.13 | — | — | — | — |
| Glycine | 75.05 | 16 | 16.9 | 19.0 | 17.9 |
| Histidine | 155.16 | 3 | 2.9 | 3.3 | 3.0 |
| Isoleucine | 131.17 | 5 | 5.2 | 5.4 | 5.3 |
| Leucine | 131.17 | 14 | 13.9 | 14.7 | 14.7 |
| Lysine | 146.19 | 14 | 19.8 | 15.6 | 15.5 |
| Methionine | 149.21 | 2 | 2.0 | 2.2 | 2.2 |
| Phenylalanine | 165.19 | 8 | 7.9 | 8.5 | 8.3 |
| Proline | 115.13 | 9 | 10.2 | 8.4 | 9.7 |
| Serine | 105.09 | 11 | 9.5 | 8.9 | 10.0 |
| Threonine | 119.12 | 7 | 6.5 | 6.8 | 6.5 |
| Tryptophan | 204.24 | 1 | N.D. | N.D. | N.D. |
| Tyrosine | 181.19 | 7 | 6.3 | 7.0 | 7.0 |
| Valine | 117.15 | 7 | 6.8 | 7.4 | 6.8 |
| Calculated Minimum Molecular Weight: | | | 17,094 | 15,794 | 16,854 |

[1] N.D. is not detected. The predicted molecular weight of bFGF is 17,124 daltons, containing 154 amino acids; i.e., lacking the amino terminal methionine. The calculated molecular weight without four cysteines and one tryptophan is 16,435.

Partial Amino Acid Sequence Analysis

Partial amino acid sequence analyses were performed with either an Applied Biosystems Inc. (ABI) Model 470A or Model 477A microsequencer. Both machines were run exclusively with ABI chemicals and standard programs, which were optimized based on the manufacturer's recommendations for each machine. Phenylthiohydantoinamino acid analysis was performed by an on-line HPLC for each machine.

The 477A was linked to an ABI Model 120A PTH Analyzer while the 470A was linked with a Hewlett- Packard Model 1090L HPLC. Both HPLC's were run exclusively with columns and solvents purchased from ABI using gradient conditions specified by ABI and adjusted to give an optimized resolution of amino acid derivatives on each instrument. Data from each HPLC were collected, stored, and integrated by a DEC Microvax II computer using A/D converters and the AccessChrom software package from Nelson Analytical, Inc. The Model 477A sequencer also stores and analyzes data with an onboard computer utilizing software supplied by ABI. In addition, pen tracings of each chromatogram were obtained with a chart recorder for manual inspection and analysis.

The results from sequencing multiple cycles of the amino terminus of three lots of intact bFGF (1, 2, 3) are presented in Table 5. These data indicate complete removal of the amino terminal methionine encoded by the plasmid DNA.

performed in 0.05M Tris-HCl buffer, pH 8.0, containing 0.0025M $CaCl_2$. Trypsin was used at a 1:100 ratio (w/w) trypsin:protein substrate. Because bulk bFGF is stored in buffer containing 1.0M NaCl, it is diluted tenfold for proteolytic digestion. Thus, depending on the initial protein concentration, the final bFGF concentration is always between 0.5 and 1.0 mg/mL. The reaction proceeded for two hours at 37° C., after which time, a second addition of trypsin was made (final ratio of trypsin to substrate of 1:50) for an additional two hours.

RP-HPLC of the resulting tryptic peptides was performed on a Spectra Physics gradient HPLC equipped with a Waters Model 490E Multiwavelength detector set at 215 nm. Chromatography employed a 4.6 mm×25 cm Vydac C-18 column. (The Separations Group, Hesperia, Calif.; Cat. #218TP54.) Two mobile phases were used to generate the gradient. Buffer A contained 0.10% (v/v) trifluoroacetic acid (TFA; Pierce Chemi-

TABLE 5
Amino-Terminal Heterogeneity of bFGF

Amino-terminal Sequence of Lot #3

| CYCLE # | 1 | 2 | 3 | 4 | 5 | 6 | 7 | 8 | 9 | 10 | |
|---|---|---|---|---|---|---|---|---|---|---|---|
| | Ala—Gly—Ser—Ile—Thr—Thr—Leu—Pro—Ala—Leu | | | | | | | | | | (27%) |
| pmoles | 199 | 41 | 64 | 94 | 68 | | 80 | 78 | 56 | 62 | |
| per residue | | | 174 | 246 | 199 | 229 | 206 | 146 | 166 | 192 | 121 |
| | Ala—Ala—Gly—Ser—Ile—Thr—Thr—Leu—Pro—Ala | | | | | | | | | | (73%) |

Amino-terminal Sequence of Lot #2

| CYCLE # | 1 | 2 | 3 | 4 | 5 | 6 | 7 | 8 | 9 | 10 | |
|---|---|---|---|---|---|---|---|---|---|---|---|
| | Ala—Gly—Ser—Ile—Thr—Thr—Leu—Pro—Ala—Leu | | | | | | | | | | (35%) |
| pmoles | 2167 | 631 | 231 | 510 | 163 | | 651 | 656 | 567 | 700 | |
| per residue | | | 2026 | 1708 | 677 | 1163 | 1919 | 1227 | 1813 | 1158 | 1316 |
| | Ala—Ala—Gly—Ser—Ile—Thr—Thr—Leu—Pro—Ala | | | | | | | | | | (65%) |

Amino-terminal Sequence of Lot #1

| CYCLE # | 1 | 2 | 3 | 4 | 5 | 6 | 7 | 8 | 9 | 10 | |
|---|---|---|---|---|---|---|---|---|---|---|---|
| | Ala—Gly—Ser—Ile—Thr—Thr—Leu—Pro—Ala—Leu | | | | | | | | | | (30%) |
| pmoles | 1246 | 405 | 156 | 285 | 285 | | 341 | 335 | 280 | 300 | |
| per residue | | | 1001 | 891 | 309 | 679 | 740 | 486 | 613 | 622 | 502 |
| | Ala—Ala—Gly—Ser—Ile—Thr—Thr—Leu—Pro—Ala | | | | | | | | | | (70%) |

The data shown are for three bulk lots of bFGF. The two amino terminal sequences are indicated with the picomoles per residue for each amino acid cycle. The (Ala—Ala—Gly . . . ) form of bFGF is consistently present at approximately 70%. (N = 3; mean = 69.3 +/−3.3)

Approximately 70% of the amino terminus begins, as expected, Ala-Ala-Gly-Ser . . . , while 30% of the amino terminus begins Ala-Gly-Ser-Ile . . . . This ratio has been consistently observed for bFGF.

Peptide Mapping

Proteolytic digestion of three lots of bFGF has been performed to provide precise evidence for the identity of the molecule. Digestion of bFGF with trypsin was cals) in water. Buffer B contained 0.09% TFA in acetonitrile (Burdick and Jackson). Both mobile phases were continuously degassed with helium. After sample injection, the column was run isocratically at 1.0 mL per minute for two minutes at 98% buffer A: 2% buffer b. Then, a gradient of one percent per minute was run from 2% to 50% buffer B. Retention times are shown in Table 6.

TABLE 6
Summary of the Actual and Relative Retention Times for Eighteen Identified Peptides Resulting from the Complete Digestion of bFGF with Trypsin.

| | T1 | T2 | T3 | T4 | T5 | T6 | T7 | T8 | T9 |
|---|---|---|---|---|---|---|---|---|---|
| Lot #1 | | | | | | | | | |
| RRT | 0.195 | 0.242 | 0.297 | 0.418 | 0.456 | 0.489 | 0.520 | 0.542 | 0.604 |
| ART | 6.29 | 7.82 | 9.60 | 13.49 | 14.74 | 15.79 | 16.8 | 17.51 | 19.53 |
| Lot #2 | | | | | | | | | |
| RRT | 0.198 | 0.241 | 0.295 | 0.415 | 0.454 | 0.487 | 0.517 | 0.539 | 0.602 |
| ART | 6.41 | 7.8 | 9.54 | 13.44 | 14.69 | 15.75 | 16.74 | 17.44 | 19.49 |
| Lot #3 | | | | | | | | | |
| RRT | 0.198 | 0.241 | 0.297 | 0.416 | 0.455 | 0.484 | 0.519 | 0.541 | 0.603 |
| ART | 6.40 | 7.79 | 9.6 | 13.46 | 14.7 | 15.66 | 16.78 | 17.5 | 19.51 |

| | T10 | T11 | T12 | T13 | T14 | T15 | T16 | T17 | T18 |
|---|---|---|---|---|---|---|---|---|---|
| Lot #1 | | | | | | | | | |
| RRT | 0.670 | 0.766 | 0.772 | 0.838 | 0.855 | 0.871 | 0.894 | 0.954 | 1.000 |

TABLE 6-continued

Summary of the Actual and Relative Retention Times for Eighteen
Identified Peptides Resulting from the Complete Digestion of bFGF
with Trypsin.

| ART Lot #2 | 21.66 | 24.74 | 24.93 | 27.08 | 27.61 | 28.13 | 28.88 | 30.83 | 32.31 |
|---|---|---|---|---|---|---|---|---|---|
| RRT | 0.667 | 0.759 | 0.766 | 0.836 | 0.854 | 0.869 | 0.892 | 0.951 | 1.000 |
| ART Lot #3 | 21.59 | 24.58 | 24.78 | 27.05 | 27.65 | 28.12 | 28.87 | 30.79 | 32.37 |
| RRT | 0.669 | 0.765 | 0.770 | 0.837 | 0.855 | 0.870 | 0.893 | 0.953 | 1.000 |
| ART | 21.63 | 24.73 | 24.91 | 27.06 | 27.64 | 28.13 | 28.89 | 30.83 | 32.34 |

Three lots of bFGF were analyzed. RP-HPLC was performed on a C-18 column using trifluoroacetic acid and acetonitrile, as described in the text.
RRT: Relative retention time based on peptide T18
ART: Actual retention time, in minutes

EXAMPLE 5

Purification of bFGF Shown by SDS-PAGE

Figure 3:
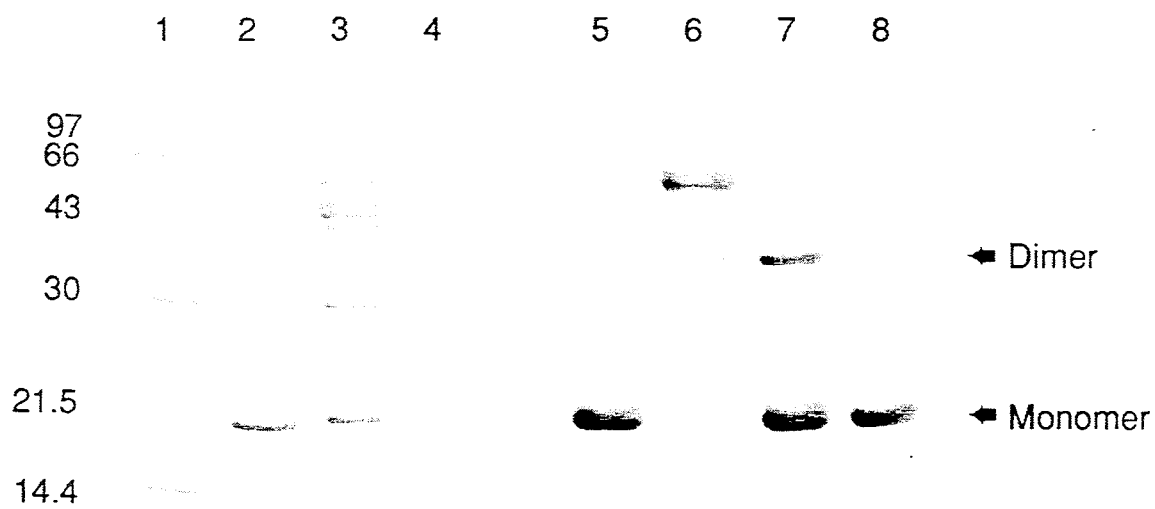
FIG. 3 is a photograph of an SDS-PAGE gel showing an analysis of bFGF fractions purified using the present invention.

FIG. 3 shows SDS-PAGE analysis of the purification process. The 15% Laemmli gel was stained with Coomassie blue. The lanes show analysis of bFGF at each step in the purification process. Samples (10 ug of protein) were reduced before electrophoresis (left panel) or applied without reduction (right panel). Arrows indicate the position of bFGF monomer and dimer. Lane 1, molecular weight standards (Pharmacia), Lane 2, bFGF standard (2 ug); lane 3, clarified cell lysate (reduced); lane 4, flow-through of sulfopropyl Sephadex (SP), reduced; lane 5, Eluate of SP column, reduced; lane 6, copper-chelate column eluate (non-reduced); lane 7, first Superose 12 column pool of high molecular weight bFGF (non-reduced); lane 8, Final bulk pool obtained after · reduction, Superose 12 chromatography, and pooling of monomeric molecular weight fractions (non-reduced).

The final bFGF pool in the purification scheme contained about 98% monomeric bFGF and about 2% dimeric bFGF as shown by non-reducing SDS-PAGE in FIG. 3. The dimer band was converted to monomer on reducing SDS-PAGE (not shown). Bulk bFGF was fully active when compared to Reference Standard bFGF in an in vitro cell proliferation assay using adrenal cortex capillary endothelial (ACE) cells as described in Example 6, infra.

EXAMPLE 6

Assays for Determining bFGF Activity

A. Adrenal Cortical Endothelial Cell Assay

In vitro biological potency of bFGF preparations was determined by measuring the mitogenic activity of each preparation in a cell proliferation assay, using adrenal cortical endothelial (ACE) cells. The assay was developed by essentially following published protocols (Gospodarowicz et al., (1986) *J. Cell Phys.*, 127:121–136; Neufeld et al., (1987) *Endocrinology*, 121:597–603). Briefly, serial dilutions of sample containing bFGF were incubated with ACE cells in culture. After a few days, the medium is removed and cell proliferation is determined by a method such as cell counting. The concentration of sample that produces half-maximal stimulation ($ED_{50}$) is determined and bFGF content calculated relative to a defined standard. Results can be seen in Table 7.

TABLE 7

| ACE Cell Proliferation Assay for In Vitro Biological Activity | |
|---|---|
| Test | $ED_{50}$* pg/ml |
| LOT 1 | 228 |
| LOT 2 | 280 |
| LOT 3 | 172 |

*$ED_{50}$ gives the amount of bFGF causing half maximal proliferation of cells.

We claim:

1. A method to recover bFGF multimers from a sample containing bFGF, said method comprising:
   applying bFGF capable of multimerization to a metal chelate affinity substrate in the absence of heparin;
   eluting from said substrate a multiplicity of fractions, some of which contain multimerized bFGF; and
   recovering multimerized bFGF from the multimerized bFGF-containing fractions.

2. The method of claim 1 wherein the metal chelate affinity substrate is selected from the group consisting of cellulose, Sepharose, Trisacryl, Silica, and Fast-Flow and cross-linked agarose derivatized to a metal ion.

3. The method of claim 2 wherein the metal ion is selected from the group consisting of copper, cobalt, iron, nickel, and zinc.

4. The method of claim 3 wherein the metal ion is cupric ion.

5. The method of claim 1 wherein said eluting is performed at a temperature from about 2° C. to about 25° C.

6. The method of claim 1 wherein the sample containing bFGF has first been partially purified by contacting an initial sample containing bFGF with a cation exchange matrix under conditions wherein said bFGF is adsorbed to said matrix, followed by eluting said bFGF from the matrix.

7. The method of claim 6 wherein the cation exchange matrix is selected from the group consisting of sulfapropyl Sephadex, sulfonated Sepharose, sulfopropyl Sepharose, Sephadex, Sepharose, silica, trisacryl and carboxymethyl cellulose.

8. The method of claim 6 wherein the steps of contacting and eluting are performed at about pH 6–8.

9. The method of claim 1 which further includes separating said bFGF multimers from a low molecular weight portion.

10. The method of claim 9 wherein said separating is conducted using a sizing gel filtration method.

11. The method of claim 10 wherein said sizing gel is selected from the group consisting of Superose 12, Sephacryl S-200, Sepharose S-300, Superdex, Trisacryl, polyacrylamide, and Sephadex.

12. The method of claim 1 which further includes treating the fractions that contain multimerized bFGF with a reducing agent so as to obtain bFGF monomers.

13. The method of claim 12 wherein the reducing agent is selected from the group consisting of dithiothreitol, 2-mercaptoethanol, cysteine, cystamine, glutathione, and dithioerythritol.

14. The method of claim 13 wherein the reducing agent is added to about a 10-fold molar excess over estimated sulfhydryl groups present in said multimerized bFGF.

15. The method of claim 12 which further includes separating said bFGF monomers from a high molecular weight portion.

16. The method of claim 15 wherein said separating is conducted using a sizing gel filtration method.

17. The method of claim 16 wherein said sizing gel is selected from the group consisting of Superose 12, Sephacryl S-200, Sepharose S-300, Superdex, Triacryl, polyacrylamide, and Sephadex.

18. The method of claim 9 which further includes treating said multimerized bFGF with a reducing agent so as to obtain bFGF monomers.

19. The method of claim 18 wherein the reducing agent is selected from the group consisting of dithiothreitol, 2-mercaptoethanol, cysteine, cystamine, glutathione, and dithioerythritol.

20. The method of claim 19 wherein the reducing agent is added to about a 10-fold molar excess over estimated sulfhydryl groups present in said multimerized 21. The method of claim 18 which further includes separating said bFGF monomers from a high molecular weight portion.

22. The method of claim 21 wherein said separating is conducted using a sizing gel filtration method.

23. The method of claim 22 wherein said sizing gel is selected from the group consisting of Superose 12, Sephacryl S-200, Sepharose S-300, Superdex, Trisacryl, polyacrylamide, and Sephadex.

24. A method to purify bFGF from a biological sample, which method comprises
    contacting said sample containing bFGF to a cation exchange matrix under conditions wherein said bFGF is adsorbed;
    eluting said bFGF from the matrix to recover a partially purified sample containing bFGF;
    applying said partially purified bFGF sample to a metal chelate affinity substrate under conditions wherein bFGF is multimerized and in the absence of heparin;
    eluting from said substrate a multiplicity of fractions, some of which contain multimerized bFGF;
    recovering multimerized bFGF from the multimerized bFGF-containing fractions;
    treating said multimerized bFGF with a reducing agent to obtain bFGF monomers; and
    separating said bFGF monomers from high molecular weight contaminants.

25. A method to purify bFGF from a biological sample, which method comprises
    applying a sample containing bFGF to a metal chelate affinity substrate under conditions wherein bFGF is multimerized and in the absence of heparin;
    eluting from said substrate a multiplicity of fractions, some of which contain multimerized bFGF;
    recovering multimerized bFGF from the multimerized bFGF-containing fractions;
    treating said multimerized bFGF with a reducing agent to obtain bFGF monomers; and
    separating said bFGF monomers from high molecular weight contaminants.

* * * * *